United States Patent
Mitani et al.

(10) Patent No.: US 8,295,657 B2
(45) Date of Patent: Oct. 23, 2012

(54) OPTICAL FIBER SENSOR AND FUEL SUPPLY APPARATUS HAVING THE SAME

(75) Inventors: Tateki Mitani, Tokyo (JP); Satoshi Nishikawa, Tokyo (JP); Shigeki Kanamaru, Tokyo (JP)

(73) Assignee: Mitsubishi Electric Corporation, Tokyo (JP)

( * ) Notice: Subject to any disclaimer, the term of this patent is extended or adjusted under 35 U.S.C. 154(b) by 371 days.

(21) Appl. No.: 12/712,666

(22) Filed: Feb. 25, 2010

(65) Prior Publication Data
US 2011/0043799 A1 Feb. 24, 2011

(30) Foreign Application Priority Data
Aug. 24, 2009 (JP) .................. 2009-193058

(51) Int. Cl.
G02B 6/00 (2006.01)
G02B 6/34 (2006.01)
(52) U.S. Cl. .............. 385/12; 385/15; 385/31; 385/37; 385/138; 356/432; 356/436
(58) Field of Classification Search .............. 385/12, 385/37; 356/432, 436
See application file for complete search history.

(56) References Cited

U.S. PATENT DOCUMENTS

| | | | | |
|---|---|---|---|---|
| 5,140,965 A * | 8/1992 | Nogi et al. | ............. | 123/494 |
| 7,151,872 B1 * | 12/2006 | Xia et al. | ............. | 385/37 |
| 7,385,692 B1 * | 6/2008 | Nguyen | ............. | 356/301 |
| 7,489,835 B1 * | 2/2009 | Xia et al. | ............. | 385/12 |
| 7,672,544 B2 * | 3/2010 | Takabayashi et al. | ............. | 385/12 |
| 7,768,646 B1 * | 8/2010 | Mentzer et al. | ............. | 356/436 |
| 8,100,586 B2 * | 1/2012 | Ruggiero et al. | ............. | 384/103 |
| 8,135,247 B2 * | 3/2012 | Xia et al. | ............. | 385/13 |
| 2005/0163424 A1 * | 7/2005 | Chen | ............. | 385/37 |
| 2006/0215959 A1 * | 9/2006 | McCarthy et al. | ............. | 385/37 |
| 2008/0204708 A1 * | 8/2008 | Shaw | ............. | 356/36 |
| 2008/0204714 A1 * | 8/2008 | Hamatani et al. | ............. | 356/72 |
| 2009/0034901 A1 * | 2/2009 | Takabayashi et al. | ............. | 385/12 |
| 2009/0129721 A1 * | 5/2009 | Chen et al. | ............. | 385/12 |
| 2010/0290733 A1 * | 11/2010 | Xia et al. | ............. | 385/12 |

FOREIGN PATENT DOCUMENTS
WO 2006/126468 A1 11/2006
* cited by examiner

Primary Examiner — Ryan Lepisto
(74) Attorney, Agent, or Firm — Sughrue Mion, PLLC (57) ABSTRACT

An optical fiber sensor includes: an optical fiber; a light source portion; and a light receiving portion. The optical fiber includes: a core that includes a grating that generates a clad mode upon receipt of light; a clad that covers the core; and a fiber jacket that covers the clad, wherein a part of the fiber jacket corresponding to an area where the grating is formed is removed so that the clad is contactable with the fuel. The light source portion includes a light cutting element that emits light, whose wavelength is within a wavelength band of the cladding mode toward the optical fiber. The light receiving portion that detects intensity of the light transmitted through the grating. The optical fiber, the light receiving portion and the light source portion are arranged linearly.

10 Claims, 8 Drawing Sheets

| FUEL TYPE | REFRACTIVE INDEX |
|---|---|
| ETHANOL | 1.3592 |
| GASOLINE (LIGHT) | 1.4210 |
| GASOLINE (HEAVY) | 1.4355 |
| E75 (v%) + GASOLINE A | 1.3724 |
| E75 (v%) + GASOLINE B | 1.3767 |
| E50 (v%) + GASOLINE A | 1.3884 |
| E50 (v%) + GASOLINE B | 1.3953 |
| E25 (v%) + GASOLINE A | 1.4050 |
| E25 (v%) + GASOLINE B | 1.4147 |

FIG. 8

OPTICAL FIBER SENSOR AND FUEL SUPPLY APPARATUS HAVING THE SAME

This application claims priority from Japanese Patent Application No. 2009-193058 filed on Aug. 24, 2009, the entire subject matter of which is incorporated herein by reference.

BACKGROUND OF THE INVENTION

1. Field of the Invention

This invention relates to an on-vehicle fuel property detection device, among members including a fuel supply apparatus, which is mounted in a fuel tank of a vehicle or the like, and which pressurizes and supplies fuel to an injector that injects fuel into an engine. Specifically, this invention relates to the detection device using an optical fiber.

2. Description of the Related Art

Recently, alcohol-blended fuel mixed with bioethanol has become widely used at an accelerated rate as an alternative to gasoline. However, in such alcohol-blended fuel, an optimum ignition timing, an optimum air-fuel ratio and the like vary with a concentration of ethanol contained in the fuel. Thus, in order to achieve appropriate engine control by a computer, i.e., an electronic control unit (ECU), it is necessary to accurately detect the concentration of alcohol contained in the fuel.

It is known, as one of means therefor, to detect the property of a liquid by an optical fiber sensor having an optical fiber, a light source and a light receiving portion (see, e.g., WO2006/126468 (Embodiment 20)). The optical fiber includes of a core having an area in which a grating is formed and a clad. The optical fiber is disposed at a position at which at least a part of the area in which the grating is formed is immersed in the liquid. The light source outputs light, whose wavelength is within a band of wavelengths of light corresponding to a cladding mode to be caused due to the grating of the area in which the grating is formed, to be incident on the optical fiber. The light receiving portion detects the intensity of light which is incident on the optical fiber from the light source and transmitted by the grating of the area.

WO2006/126468 discloses that the property of fuel stored in a fuel tank is accurately detected by providing an optical fiber probe in the fuel tank (in the case of Embodiment 20) or outside the fuel tank (in the case of Embodiment 19). Between these cases, the case of providing the optical sensor probe in the fuel tank as in Embodiment 20 has an advantage in that the detected property is insusceptible to temperature and heat, as compared with the case of providing the optical sensor probe outside the fuel tank, more particularly, in the vicinity of a vehicular engine room. However, on the other hand, the optical fiber used in the optical sensor probe described in WO2006/126468 is bent like a letter "U" regardless of which of the transmission type and the reflection type the optical fiber sensor is. The influence of the bending of the optical fiber superimposes on the properties of the fuel. Consequently, the optical fiber sensor described in WO2006/126468 has a problem of increasing an error of the detected properties.

SUMMARY OF THE INVENTION

The invention is accomplished to solve the above problem. An object of the invention is to obtain an on-vehicle fuel property detection device using an optical fiber sensor, which reduces a detection error of detected properties while a structure, in which an optical fiber sensor is provided in a fuel tank, in order to make the properties insusceptible to temperature and heat.

According to one aspect of the invention, there is provided an optical fiber sensor, which is provided in a fuel tank of a vehicle, and which detects a property of fuel in the fuel tank, the optical fiber sensor comprising: an optical fiber comprising: a core that comprises a grating that generates a clad mode upon receipt of light; a clad that covers the core; and a fiber jacket that covers the clad, wherein a part of the fiber jacket corresponding to an area where the grating is formed is removed so that the clad is contactable with the fuel; a light source portion comprising a light cutting element that emits light, whose wavelength is within a wavelength band of the cladding mode toward the optical fiber; and a light receiving portion that detects intensity of the light transmitted through the grating, wherein the optical fiber, the light receiving portion and the light source portion are arranged linearly.

As described above, according to the invention, the on-vehicle fuel property detection device can be obtained, which uses the optical fiber sensor that is compact and has a simple structure, and that accurately measures the concentration of alcohol contained in fuel without being affected by temperature and heat.

DETAILED DESCRIPTION OF THE PREFERRED EMBODIMENTS

Embodiment 1

Figure 1:
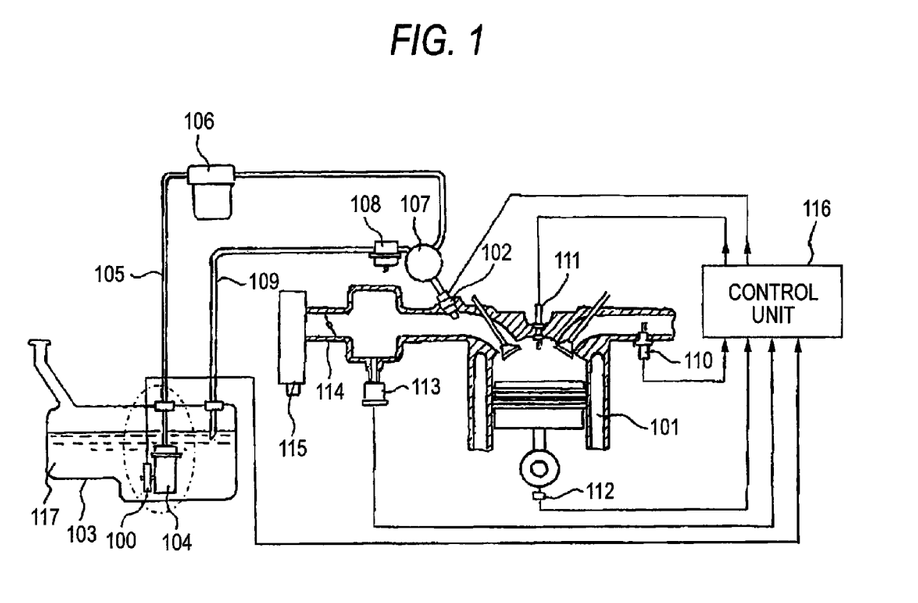
FIG. 1 is a diagram illustrating the configuration of an on-vehicle fuel control system according to Embodiment 1 of the invention.

An object of the invention is to accurately detect a concentration of alcohol contained in fuel in order to achieve appropriate ECU control. First, upon describing a mechanism for measuring the concentration of alcohol contained in fuel, a configuration and an operation of an entire fuel control system are first described with reference to FIG. 1. FIG. 1 is a diagram illustrating the configuration of an on-vehicle fuel control system.

In FIG. 1, reference numeral 100 designates a fuel property detection device (hereinafter referred to as an optical fiber sensor) implemented by an optical fiber sensor. Reference numeral 101 designates an engine of an automobile or the like. Reference numeral 102 designates a fuel injection valve. Reference numeral 103 designates a fuel tank. Reference numeral 104 designates a fuel pump. Reference numeral 106 designates a high-pressure filter for filtering fuel 117 sucked up from the fuel pump 104 via a fuel supply pipe 105. Reference numeral 107 designates a fuel distribution pipe. Reference numeral 108 designates a fuel pressure regulator. Reference numeral 109 designates a fuel return pipe. Reference numeral 110 designates an air-fuel-ratio sensor. Reference numeral 111 designates an ignition plug. Reference numeral 112 designates an engine speed sensor. Reference numeral 113 designates an intake pressure sensor. Reference numeral 114 designates a throttle valve. Reference numeral 115 designates an air cleaner. Reference numeral 116 designates a control unit including an ECU, to which signals output from the optical fiber sensor 100, the air-fuel-ratio sensor 110, the engine speed sensor 112, the intake pressure sensor 113, and the like are input. The control unit 116 drives the fuel injection valve 102, the ignition plug 111, and the like, based on controlled variables corresponding to the input signals.

Next, a series of operations of the fuel control system are described hereinafter. When the fuel 117 is supplied to the fuel tank 103, the engine 101 is started. Simultaneously, the fuel 117 is pressurized by the fuel pump 104. Thus, the fuel 117 flows into the fuel distribution pipe 107 through the fuel supply pipe 105 and the high-pressure filter 106. Apart of the fuel 117 is supplied to the engine 101 from the fuel injection valve 102. The rest of the fuel 117 is returned to the fuel tank 103 through the fuel pressure regulator 108 and the fuel return pipe 109. Incidentally, the fuel pressure regulator 108 always maintains the pressure of the fuel 117 in the pipes up to the fuel distribution pipe 107 at a constant value, regardless of an amount of fuel consumption of the fuel injection valve 102. The presence/absence of alcohol mixed in the fuel 117 is detected by the optical fiber sensor 100 attached to the fuel pump 104. When alcohol mixed in the fuel is present, the rate of content of alcohol is measured by the optical fiber sensor 100, as will be described below. When the measured rate of content of alcohol is input to the control unit 116, the control unit 116 grasps the state of the engine according to signals output from the engine speed sensor 112 and the intake pressure sensor 113, and the control unit 116 changes an amount of fuel supplied to the engine by controlling the valve opening time of the fuel injection valve 102. On the other hand, an air-fuel ratio is detected by the air-fuel-ratio sensor 110. The control unit 116 performs the feedback control of the air-fuel-ratio so that the air-fuel-ratio reaches a target value corresponding to the state of the engine at that time. In addition, the control unit 116 controls the ignition timing of the ignition plug 111 according to the state of the engine. Accordingly, optimum engine control according to the type of fuel supplied to a vehicle becomes possible.

Figure 2:
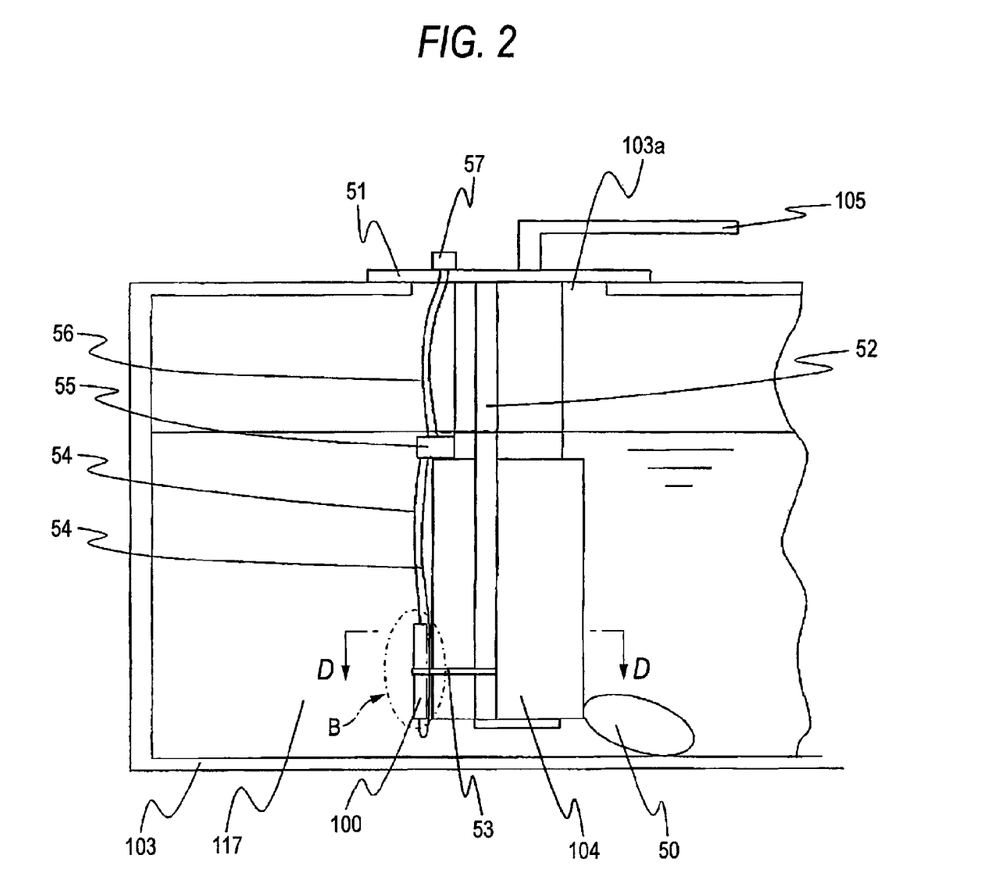
FIG. 2 is a diagram detailedly illustrating an A-portion shown in FIG. 1.

Next, the attachment of the optical fiber sensor 100 to the fuel pump 104 is described below with reference to FIG. 2. Incidentally, FIG. 2 is a diagram detailedly illustrating an A-portion shown in FIG. 1, what is called a fuel supply apparatus. As illustrated in FIG. 2, the fuel pump 104 sucks and pressurizes the fuel 117 through a filter 50 and feeds the pressurized fuel 117 into the fuel injection valve 102 (see FIG. 1, that is a part of injector) through the fuel supply pipe 105. Generally, when the fuel pump 104 is mounted in the fuel tank 103, the fuel pump 104 is removably supported therein by a stay 52 fixed to a plate 51 that blocks a hole 103a provided in the fuel tank 103. The stay 52 is provided with an arm 53 on which the optical fiber sensor 100 is provided so that the direction of the optical fiber sensor 100 is perpendicular to a liquid surface of the fuel 117.

A pair of sensing lines 54 respectively extending from a light source portion 3 and a light receiving portion 5 (to be described below) provided in the optical fiber sensor 100 are connected to a control portion 55 in which signals from the sensing lines 54 are converted into optimum signals representing the property of the fuel 117. Then, the optimum signals are connected via a signal line 56 to a connector 57 which is connected to the control unit 116. The pair of sensing lines 54 differs in length between the optical fiber sensor 100 and the control portion 55 from each other due to the structure of the optical fiber sensor 100. In FIG. 2, the control portion 55 is added to the fuel pump 104 such that the control portion 55 is one member including the fuel supply apparatus. Alternatively, the control portion 55 may be installed in or outside the fuel tank 103. For example, when the fuel tank 103 is installed in the fuel tank 103, the number of members can be reduced by incorporating the function of the connector 57 to the control portion 55. The fuel supply apparatus maybe configured by incorporating the high-pressure filter 106 and the fuel pressure regulator 108 illustrated in FIG. 1 thereinto, i.e., in the form of what is called a fuel pump module. Specifically, when the fuel pressure regulator 108 is incorporated into the fuel supply apparatus, the fuel is not returned to the fuel tank 103 through the fuel return pipe 109, and thus this case has a merit that the temperature resistance of the optical fiber sensor 100 can be improved.

Figure 3:
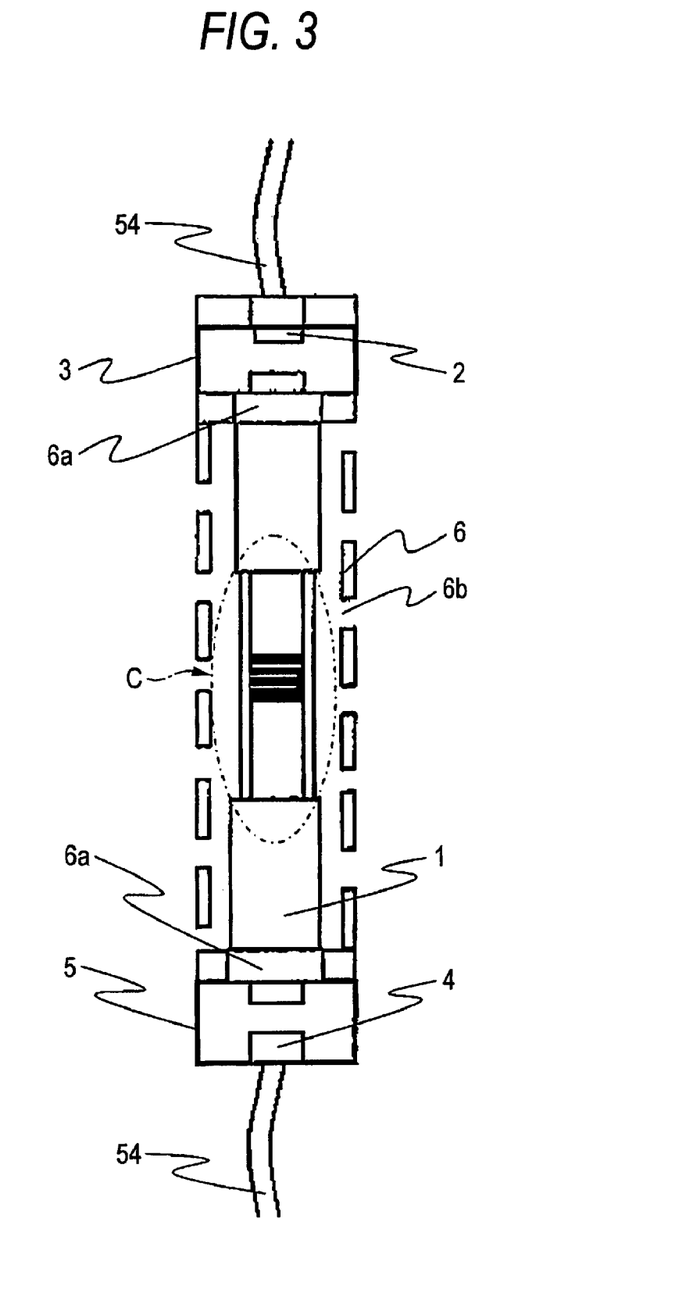
FIG. 3 is an enlarged diagram of a B-portion shown in FIG. 2, which illustrates an optical fiber sensor.
Figure 4A:
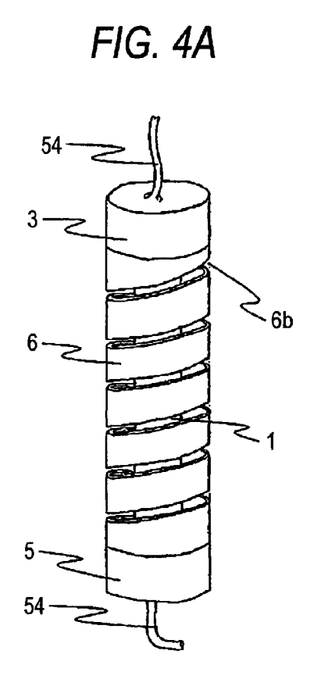
FIGS. 4A to 4C are perspective diagrams illustrating the appearance of the B-portion shown in FIG. 3.
Figure 4B:
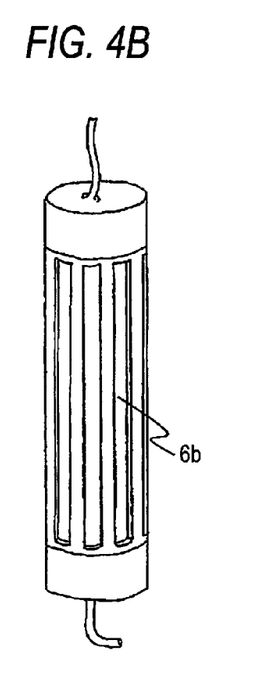
Figure 4C:
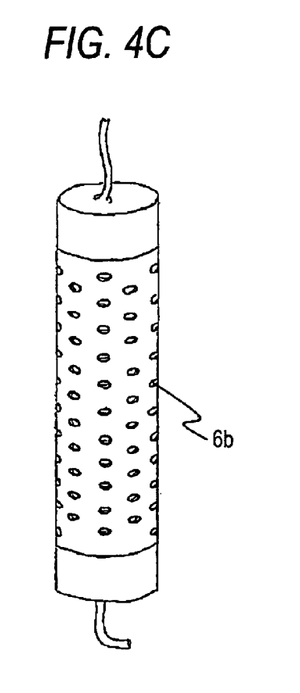

Next, the internal structure of the optical fiber sensor 100 is described hereinafter with reference to FIGS. 3 to 4C. FIG. 3 is an enlarged diagram of a B-portion shown in FIG. 2. FIGS. 4A to 4C are perspective diagrams illustrating the appearance of the B-portion shown in FIG. 3. In FIG. 3, reference numeral 1 designates an optical fiber. Reference numeral 3 designates a light source portion including a light emitting element 2 disposed at a first end portion of the optical fiber 1. Reference numeral 5 designates a light receiving portion including a light receiving element 4 disposed at a second end portion of the optical fiber 1. A light emitting diode, a laser diode or the like can be used as the light emitting element 2. A spectral analyzer, a photodiode or the like can be used as the light receiving element 4. The light source portion 3 and the light receiving portion 5 are airtightly connected to the optical fiber 1 penetrating through opening portions 6a of a pipe 6. The light source portion 3 and the light receiving portion 5 are immersed in the fuel 117, as shown in FIG. 2. Thus, each of the light source portion 3 and the light receiving portion 5 has an airtight structure.

The airtight structure is obtained by performing a welding connection of each of the opening portions 6a or by applying a fusion structure using glass thereon. Preferably, each of the opening portions 6a functioning as a part of a connection portion is sealed with low-melting-point glass by way of example. Preferably, the pipe 6 is formed of metal when the opening portions 6a are sealed. In addition, in consideration of the fact that the pipe 6 is immersed in the fuel 117, similarly to the light source portion 3 and the light receiving portion 5, preferably, the pipe 6 is formed of a stainless steel. Obviously, it is necessary that the optical fiber 1 is contacted with the fuel 117. Thus, as shown in FIG. 3 or FIG. 4A, the pipe 6 can maintain the continuity thereof (in plain words, the pipe 6 can hold the optical fiber 1) by providing a spiral fuel introduction hole 6b therein. The fuel introduction hole 6b may be formed into a shape illustrated in FIG. 4B or 4C. Specifically, the shape illustrated in FIG. 4C facilitates forming the pipe 6 of resin and reduction in weight of the optical fiber sensor 1. When the pipe 6 is formed of resin, it is useful that the sealing of the opening portions 6a with low-melting-point glass is performed at the light source portion 3 and the light receiving portion 5, and that the light sealing portion 3 and the light receiving portion 5 are connected to the pipe 6 by, e.g., screwing. Even when the pipe 6 is formed of resin, similarly in consideration of the fact that the pipe 6 is immersed in the fuel 117, preferably, the material of the pipe 6 is a polyacetal resin.

Figure 5:
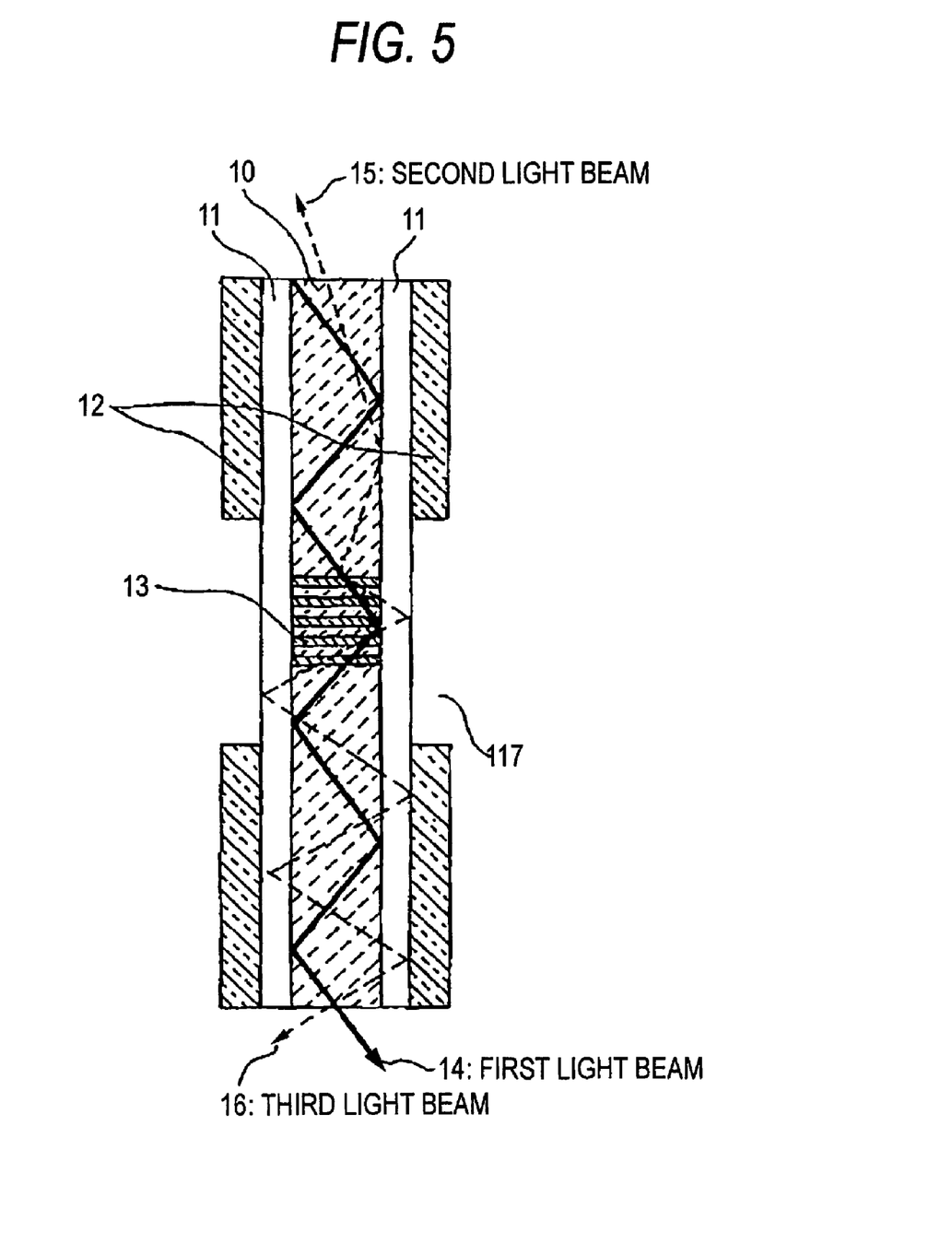
FIG. 5 is an enlarged diagram of a C-portion shown in FIG. 3.

Hereinafter, a principle of detecting the property of fuel is described with reference to FIGS. 5 to 7. Incidentally, FIG. 5 is an enlarged diagram of a C-portion shown in FIG. 3.

Figure 6:
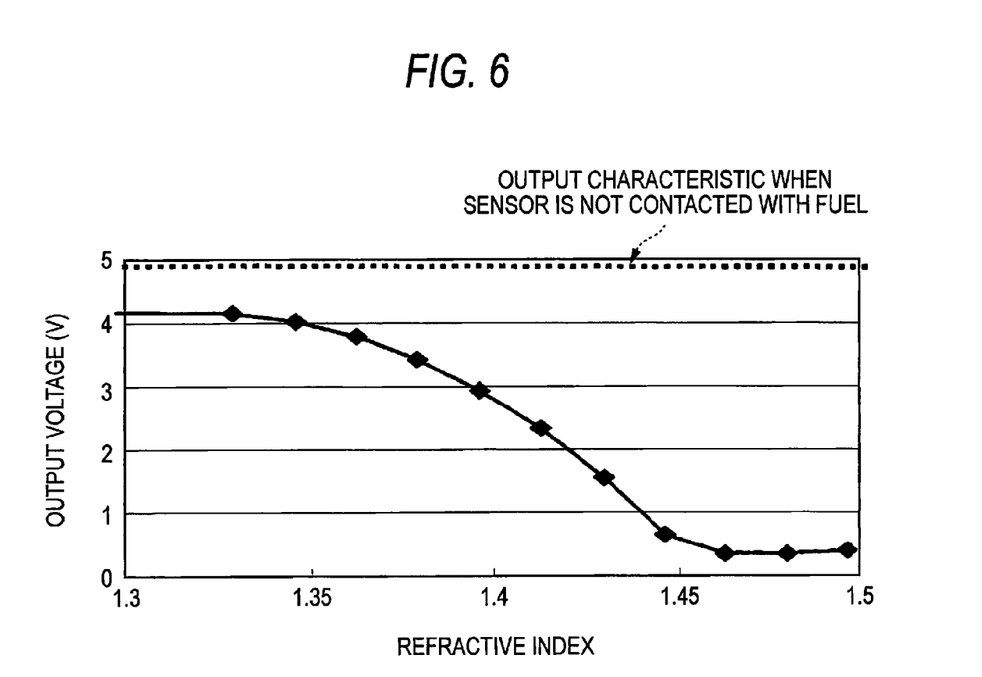
FIG. 6 is a graph illustrating an output characteristic of the optical fiber sensor according to Embodiment 1 of the invention.
Figure 7:
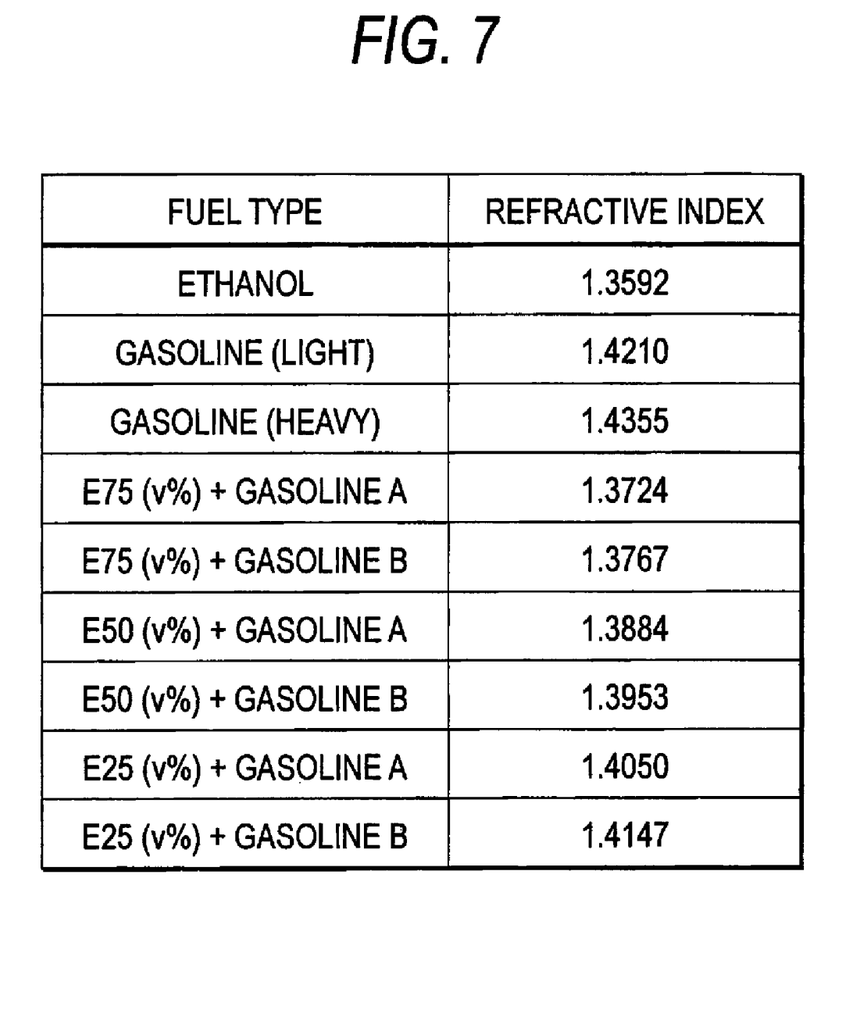
FIG. 7 is a table illustrating the refractive index of fuel.

FIG. 6 is a graph illustrating an output characteristic of the optical fiber sensor. FIG. 7 is a table illustrating the refractive index of fuel. The optical fiber 1 includes a core 10 in which light emitted from the light source portion 3 (see FIG. 3) propagates, a clad 11 which covers the core 10 to confine light in the core 10, and a fiber jacket 12 covering the core 10 and the clad 11 for protection. In order to detect the property of the fuel 117 around the optical fiber sensor 100, a part of the fiber jacket 12 is removed so that the clad 11 is contacted directly with the fuel 117. Inorganic glass such as quartz glass, or plastic materials such as polymethylmethacrylate, can be used as the materials of the core 10 and the clad 11. A highly gasoline-resistant resin, such as a fluororesin, can be used as the material of the fiber jacket 12.

The principle of detecting the property of fuel utilizes a phenomenon that the intensity of a light beam in "a cladding mode" caused when a grating 13 reflects or transmits the light beam propagating in the core 10, which varies depending upon the refractive index of fuel contacted with an outer peripheral part of the clad 11. That is, in a part of the core 10 not formed the grating 13 the light beam propagating therein repeats reflection on the boundary surface between the core 10 and the clad 11, so that the light beams propagate only in the core 10. However, when the light beam reaches the grating 13, the light beam is split into a first light beam 14 which is transmitted by the grating 13 and propagates in the core 10, a second light beam 15 which undergoes a Bragg reflection at the grating 13 and propagates in the core 10 in a opposite direction, and a third light beam 16 which leaks out of the core 10 and propagates in the clad 11. The intensity of the first light beam 14 which is transmitted through the grating 13 and propagates in the core 10, and the third light beam 16 which leaks out of the core 10 and propagates in the clad 11, can be detected by the light receiving portion 5 (see FIG. 3) located at the second end of the optical fiber 1 in the direction of propagation of the light beams.

Here, the wavelength characteristic curve of the intensity of the transmitted light in the cladding mode has periodic loss peaks. Because the optical fiber 1 is immersed in the fuel 117, the height of each periodic loss peak varies depending upon the refractive index of the fuel 117. In the alcohol-blended fuel, it has already been known that the refractive index of the fuel varies depending upon the concentration of ethanol contained in the fuel, shown in FIG. 7. Thus, it is detected that the loss peaks of the transmission spectra of light in the cladding mode vary depending on the refractive index of the fuel, the concentration of alcohol contained in the fuel can be estimated by detecting the refractive index of the liquid.

That is, a total amount of the intensity of light transmitted through the grating 13 changes depending upon the property (refractive index) of the fuel contacted with the outer peripheral part of the clad 11. Accordingly, the property (refractive index) of the fuel can be detected by an amount of light received by the light receiving element 4. The control portion 55 (see FIG. 3) converts the amount of light detected by the light receiving element 4 into a voltage signal and outputs the voltage signal. As shown in FIG. 6, an output voltage (V) of the control portion 55 has a substantially inverse proportion relationship with the refractive index of the fuel. That is, as shown in FIGS. 6 and 7, when the concentration of alcohol contained in the fuel increases, the refractive index of the fuel decreases, while the output voltage increases. An estimated value of the refractive index is calculated from the value of the output voltage (V) of the control portion 55. Specifically, the refractive index is estimated from the output voltage. Then, the properties of the fuel, e.g., the presence/absence of alcohol mixed in the fuel and the rate of content of the alcohol when the alcohol mixed in the fuel is present, can be grasped by the estimated refractive index. In other word, because such an output voltage corresponding to such a refractive index of the fuel is obtained, the valve opening time of the fuel injection valve 102 and the ignition timing of the ignition plug 111 are controlled according to such an output voltage. Consequently, optimal engine control can be implemented.

The shape of the optical fiber sensor 100, which results in the optimal engine control, is described hereinafter in more detail. As is apparent from FIGS. 2 and 3 that have already been described, the optical fiber sensor 100 is configured so that the light source portion 3 and the light receiving portion 5 in addition to the optical fiber 1 are immersed in the fuel 117. Because it is unnecessary to bend the optical fiber 1, an error of the output voltage obtained corresponding to the property of the fuel is extremely small. The light source portion 3 and the light receiving portion 5 need to maintain airtightness. However, because the light source portion 3 and the light receiving portion 5 are immersed in the fuel, change in the temperature thereof is relatively small. Accordingly, the invention can have a considerable ripple effect that a sensor stable in temperature is obtained.

Figure 8:
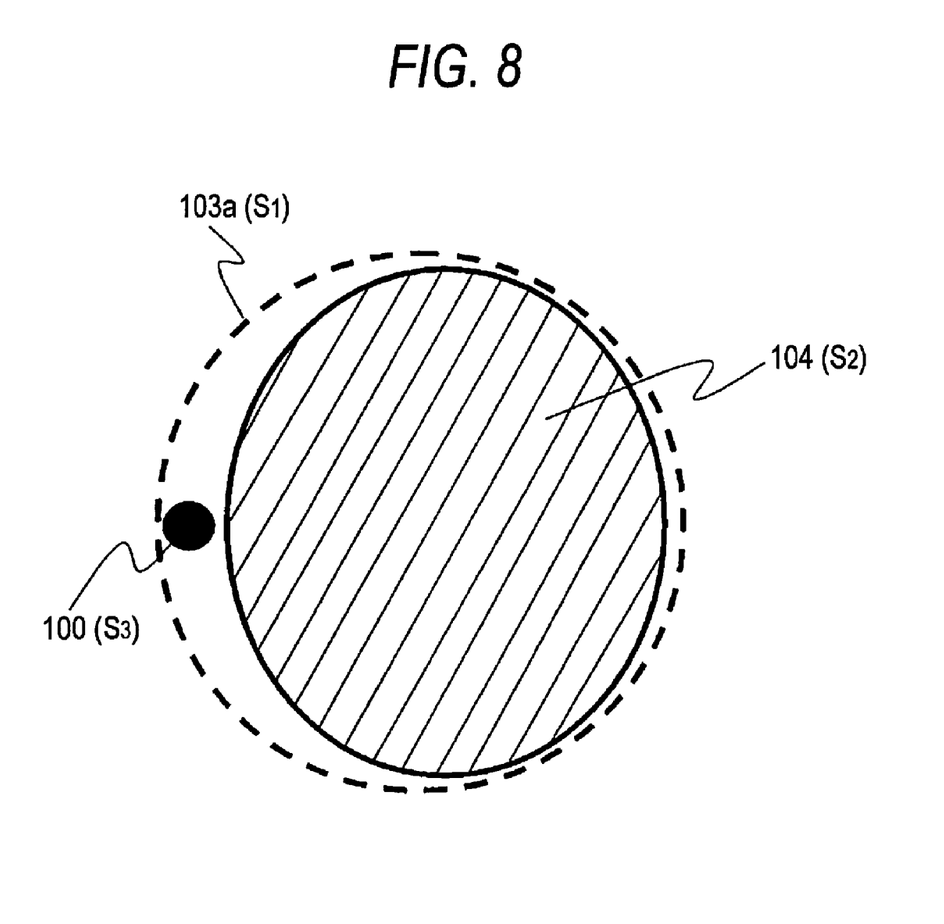
FIG. 8 is cross-sectional diagram taken along line D-D shown in FIG. 2.

Because the optical fiber sensor 100 is attached to the arm 53 installed on the stay 52, when the optical fiber sensor 100 is immersed in the fuel, an immersing operation is very easily achieved. When the optical fiber sensor 100 is attached to the fuel pump 104, the fuel pump 104 and the optical fiber sensor 100 according to the invention are configured such that the area of a projection of the fuel pump 104 and the optical fiber sensor 100 on a plane including the hole 103a is less than the area of the hole 103a as shown in FIG. 8.That is, the area ($S_3$) of a cross-section of the optical fiber sensor 100 is less than a value obtained by subtracting the area ($S_2$) of a maximum cross-section part of the fuel pump 104 from the area ($S_1$) of the hole 103a. Thus, even in the case of a fuel supply apparatus having a fuel property detection device, the fuel supply apparatus can smoothly be mounted in the fuel tank 103 without being damaged.

Hereinafter, another embodiment will be described. The relationship between the output voltage of the optical fiber sensor 100 and the refractive index of the fuel 117 has shown in FIG. 6. For example, when the fuel is not contacted with the grating 13, an output voltage having an output characteristic curve indicated with a dashed line added to FIG. 6 is obtained. When the output voltage which is about 5 V is input to the control portion 55, the output voltage can be used to turn on an alarm lamp indicating occurrence of a "small-remaining-fuel-amount" state in which the liquid level of the fuel contained in the fuel tank 103 is lower than the position of the optical fiber sensor 100.

The optical fiber sensor 100 according to the invention has been described as a member of the fuel supply apparatus attached to the fuel pump 104. However, the mode for carrying out the invention is not limited thereto. For example, even when the optical fiber sensor 100 is used in a stand-alone mode, similarly to shown in FIG. 41 of WO2006/126468, it is apparent that the advantages can similarly be obtained. In addition, although the optical fiber sensor 100 has been described as a fuel property detection device, similarly, it is apparent that the optical fiber sensor 100 can be applied to a liquid level detection device by causing the optical fiber sensor 100 itself extending in a direction perpendicular to the liquid surface of the fuel.

While the invention has been shown and described with reference to certain exemplary embodiments thereof, it will be understood by those skilled in the art that various changes in form and details may be made therein without departing from the spirit and scope of the invention as defined by the appended claims.

What is claimed is:

1. An optical fiber sensor, which is provided in a fuel tank of a vehicle, and which detects a property of fuel in the fuel tank, the optical fiber sensor comprising:
    an optical fiber comprising:
        a core that comprises a grating that generates a clad mode upon receipt of light;
        a clad that covers the core; and
        a fiber jacket that covers the clad,
            wherein a part of the fiber jacket corresponding to an area where the grating is formed is removed so that the clad is contactable with the fuel;
    a light source portion comprising a light cutting element that emits light, whose wavelength is within a wavelength band of the cladding mode toward the optical fiber; and
    a light receiving portion that detects intensity of the light transmitted through the grating,
    wherein the optical fiber, the light receiving portion and the light source portion are arranged linearly, and
    wherein at least one of the light source portion and the light receiving portion are immersed in the fuel.

2. The optical fiber sensor according to claim 1, wherein each of the light source portion and the light receiving portion has an airtight structure.

3. The optical fiber sensor according to claim 2, wherein the airtight structure of each of the light source portion and the light receiving portion is obtained by sealing a connection portion between the optical fiber and each of the light source portion and the light receiving portion with low-melting-point glass.

4. The optical fiber sensor according to claim 1, wherein the light source portion and the light receiving portion are immersed in the fuel.

5. The optical fiber sensor according to claim 1, further comprising:
    a pipe that covers the fiber jacket to hold the optical fiber.

6. The optical fiber sensor according to claim 5, wherein the pipe comprises an opening portion at the end potion thereof and a fuel introduction hole on a side portion thereof.

7. The optical fiber sensor according to claim 1, wherein the grating is formed substantially central portion of the optical fiber.

8. A fuel supply apparatus comprising:
    an optical fiber sensor, which is provided in a fuel tank of a vehicle, and which detects a property of fuel in the fuel tank, the optical fiber sensor comprising:
        an optical fiber comprising:
            a core that comprises a grating that generates a clad mode upon receipt of light;
            a clad that covers the core; and
            a fiber jacket that covers the clad,
                wherein a part of the fiber jacket corresponding to an area where the grating is formed is removed so that the clad is contactable with the fuel;
        a light source portion comprising a light cutting element that emits light, whose wavelength is within a wavelength band of the cladding mode toward the optical fiber; and
        a light receiving portion that detects intensity of the light transmitted through the grating,
        wherein the optical fiber, the light receiving portion and the light source portion are arranged linearly,
        wherein the optical fiber sensor is provided in a fuel pump module having a fuel pump that supplies the fuel from the fuel tank to an injector of the vehicle,
        wherein an area of a projection of a combination of the optical fiber sensor and the fuel pump module on a plane including an hole provided in the fuel tank for mount the fuel pump in the fuel tank is less than an area of the hole,
        wherein at least one of the light source portion and the light receiving portion are immersed in the fuel.

9. The fuel supply apparatus according to claim 8, wherein the light source portion and the light receiving portion are immersed in the fuel.

10. An optical fiber sensor, which is provided in a fuel tank of a vehicle, and which detects a property of fuel in the fuel tank, the optical fiber sensor comprising:
    an optical fiber comprising:
        a core that comprises a grating that generates a clad mode upon receipt of light;
        a clad that covers the core; and
        a fiber jacket that covers the clad,
            wherein a part of the fiber jacket corresponding to an area where the grating is formed is removed so that the clad is contactable with the fuel;
    a light source portion comprising a light cutting element that emits light, whose wavelength is within a wavelength band of the cladding mode toward the optical fiber; and
    a light receiving portion that detects intensity of the light transmitted through the grating,
    wherein the optical fiber, the light receiving portion and the light source portion are arranged along a continuous line, and
    wherein at least one of the light source portion and the light receiving portion are immersed in the fuel.

* * * * *